US00PP09990P

United States Patent [19]

Fruehwirth

[11] Patent Number: Plant 9,990

[45] Date of Patent: Aug. 5, 1997

[54] POINSETTIA PLANT NAMED 'VARIEGATED-LEAF SUCCESS'

[75] Inventor: Franz Fruehwirth, Encinitas, Calif.

[73] Assignee: Paul Ecke Ranch, Inc., Encinitas, Calif.

[21] Appl. No.: 621,002

[22] Filed: Mar. 22, 1996

[51] Int. Cl.[6] ..... A01H 5/00

[52] U.S. Cl. ..... Plt./86.4

[58] Field of Search ..... Plt./86.4, 86.1

*Primary Examiner*—Howard J. Locker

*Attorney, Agent, or Firm*—Arnold, White & Durkee

[57] ABSTRACT

Poinsettia 'Variegated-Leaf Success' is a new cultivar, distinguished by bright red flower bracts, variegted multi-colored foliage, and self-branching characteristics. 'Variegated-Leaf Success' is a sport of the poinsettia '559' (U.S. Plant Pat. No. 8,773) with the same cultural requirements. It has a shorter growth habit than '559'. The new plant produces a unique branched pot plant.

2 Drawing Sheets

BACKGROUND OF THE NEW PLANT

This new poinsettia cultivar, 'Variegated-Leaf Success,' originated as a natural sport of poinsettia '559' (U.S. Plant Pat No. 8,773). It appeared among several thousand '559' plants in my greenhouse in Encinitas, Calif. in 1994. It was selected because of its striking, multi-colored foliage and bright red flower bracts, traits that distinguish it from other poinsettia cultivars, and seem to make it a desirable plant for commercial greenhouse production. After selection, 'Variegated-Leaf Success' was vegetativley reproduced from stem cuttings for test purposes in Encinitas, Calif. By subjecting clones of this plant to successive generations of vegetative propagation, it was demonstrated that the distinctive characteristics of 'Variegated-Leaf Success' held true from generation to generation.

DESCRIPTION OF THE PHOTOGRAPHS

Poinsettia 'Variegated-leaf Success' is illustrated in the accompanying color photographs.

DESCRIPTION OF THE PLANT

Figure 1:
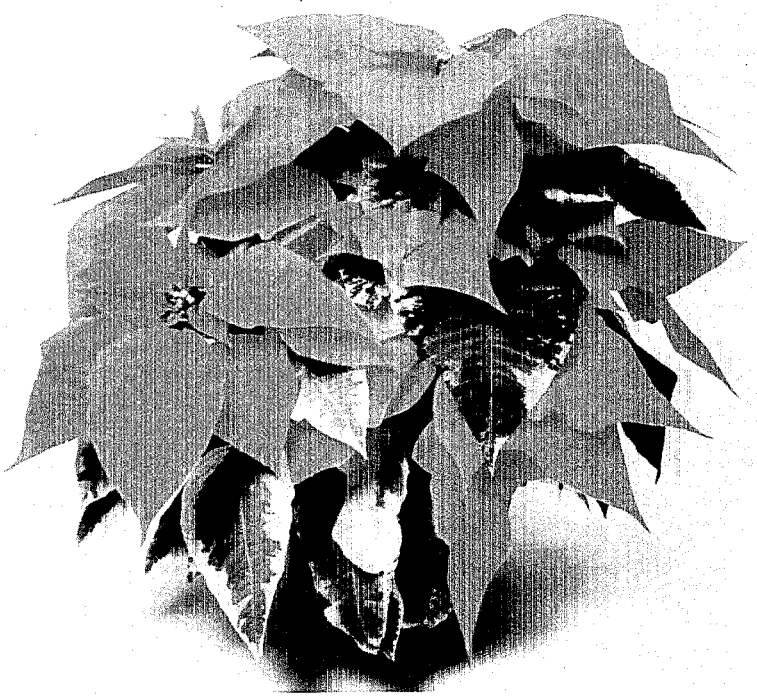
FIG. 1 is a side view of one branched plant per pot in full flower.
Figure 2:
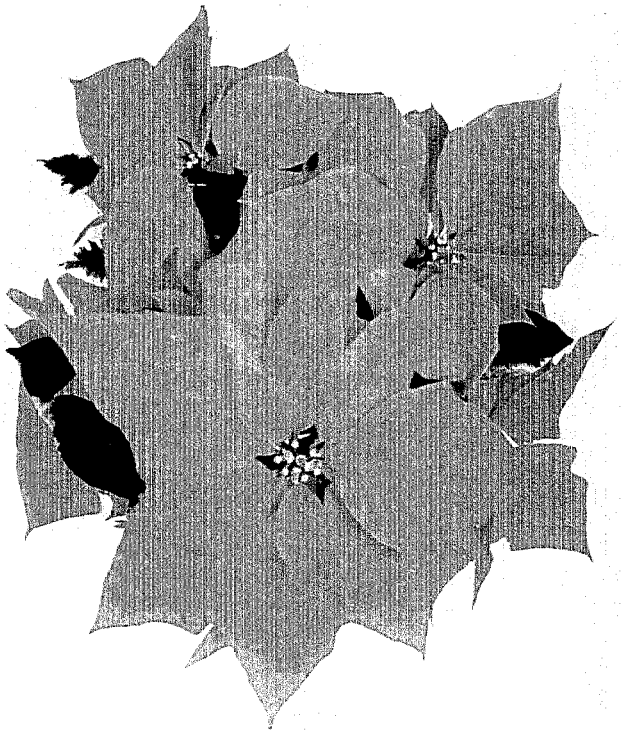
FIG. 2 is a top view of the same plant showing flower and bract formation.

The following is a detailed description of this new poinsettia as observed in Encinitas, Calif., USA during December 1995. Observations were recorded from flowering plants, grown as one branched plant per pot. The pot was 14 cm in diameter and 11 cm in height. Color designations are compared to the 1986 edition of R.H.S. Color Chart, first published in 1966 by The Royal Horticultural Society, London, England.

DESCRIPTION OF THE PLANT

The following is a detailed description of this new poinsettia as observed in Encinitas, Calif., USA during December 1995. Observations were recorded from flowering plants, grown as one branched plant per pot. The pot was 14 cm in diameter and 11 cm in height. Color designations are compared to the 1986 edition of R.H.S. Color Chart, first published in 1966 by The Royal Horticultural Society, London, England.

THE PLANT

Origin: Naturally occuring sport of poinsettia '559' (U.S. Plant Pat No. 8,773).

Classification:

*Botanical.*—*Euphorbia pulcherrima Willd.*

*Common name.*—Poinsettia.

*Cultivar name.*—'Variegated-Leaf Success'.

Form: Shrub.

Height: Short.

Growth habit: As a Single stemmed plant, upright and vigorous with self-branching side shoots. The cultural requirements appear to be the same as for the parent, poinsettia '559'. The application of a chemical growth retardant may not be needed because 'Variegated-Leaf Success' does not grow as tall as '559'. I observed a branched plant in a pot with an overall height of 38 cm and an overall width of 45 cm. The bract diameter of individual flowers was 33 cm. By contrast, at "full flower" cultivar '559'had an overall height of 43 cm.

Branching: Axillary branches will develop and terminate in a flower without pinching. However, it is usually desirable to pinch 'Variegated-Leaf Success' before flower induction and remove all terminal dominance. Then, all axillary branches will develop uniformly and at a faster rate.

Growth rate: Rooting of stem cuttings occurs in 12–18 days under intermittent mist. The plant will flower in about ten weeks under continuous long night conditions and night temperatures 16–18 degrees C.

Foliage: The foliage is variegated with irregular areas of sometimes 2 but mostly 3 different colors in the same leaf. The colors may be generally described as dark green, light green and light yellow. The yellow color is usually at the periphery of the leaf blades. The leaves are of medium size, leaf blades typically being 15–16 cm long and 10–11 cm wide with leaf petioles 5–6 cm long.

*Leaf shape.*—Typical leaves are generally ovate with obtuse bases and acuminate tips. Leaf margins are mostly entire.

*Color.*—Upper side — Dark green, darker R.H.S. 147A. Light green, near R.H.S. 148B. Yellow, lighter than R.H.S. 153D.

*Retention.*—The foliage lasts well even under low light intensities in the consumer's home.

Bracts: Generally there are 12–15 bright red bracts of various sizes subtending the cyathia. The primary bracts are medium to large, having blades typically 18 cm long and 12 cm wide with petioles 2 cm long.

*Shape.*—Bracts are ovate with acute bases and acuminate tips. Primary bract margins are lobed with one indentation on either side of the bract. Secondary bracts are ovate to elliptic and have entire margins.

*Color.*—Upper side—Bright red, near R.H.S. 45B. Under side—Red, near R.H.S. 46C.

Flowers: Generally, 10–12 cyathia (flowers) were present when the plant was in full bloom. Each cyathium is about 6 mm long and 5 mm wide, green in color, and fringed with red at the distal end. A yellow nectar cup protrudes from the side of each cyathium. The flower pedicel is also green and about 5 mm in length. The stamens protruding from the cyathia are red. The anthers are bifurcate; the pollen is yellow and copious. The stigmas are red and trifurcate.

*Nectar exucate.*—Present, abundant.

*Seed formation.*—Self-incompatible.

*Fertiligy.*—Not observed.

Post production: 'Variegated-Leaf Success' was resistant to epinasty after being confined to shipping containers. The foliage and bract retention were good.

What is claimed is:

1. A new and distinct cultivar of poinsettia plant, substantially as herein shown and described, distinguished by its variegated tri-colored foliage, bright red flower bracts and self branching traits.

* * * * *